(12) United States Patent
Ramasubramanian et al.

(10) Patent No.: US 8,962,531 B2
(45) Date of Patent: Feb. 24, 2015

(54) DEVELOPMENT OF A HIGH-THROUGHPUT SCREEN FOR THE IDENTIFICATION OF NOVEL ANTIFUNGAL DRUG CANDIDATES

(75) Inventors: Anand K. Ramasubramanian, San Antonio, TX (US); Jose L. Lopez-Ribot, San Antonio, TX (US); Anand Srinivasan, San Antonio, TX (US); Priya Uppuluri, Rancho Santa Margarita, CA (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/522,446

(22) PCT Filed: Jan. 14, 2011

(86) PCT No.: PCT/US2011/021407
§ 371 (c)(1),
(2), (4) Date: Oct. 15, 2012

(87) PCT Pub. No.: WO2011/088401
PCT Pub. Date: Jul. 21, 2011

(65) Prior Publication Data
US 2013/0040854 A1 Feb. 14, 2013

Related U.S. Application Data

(60) Provisional application No. 61/295,428, filed on Jan. 15, 2010.

(51) Int. Cl.
| C40B 30/06 | (2006.01) |
| C40B 50/06 | (2006.01) |
| C40B 40/02 | (2006.01) |
| G01N 33/569 | (2006.01) |

(52) U.S. Cl.
CPC ............................... *G01N 33/56961* (2013.01)
USPC .................... 506/10; 506/14; 506/26

(58) Field of Classification Search
CPC .......... C40B 30/06; C40B 40/02; C40B 50/06
USPC ...................................................... 506/10, 14
See application file for complete search history.

(56) References Cited

U.S. PATENT DOCUMENTS

| 5,474,915 A | 12/1995 | Dordick |
| 5,618,933 A | 4/1997 | Dordick et al. |
| 5,854,030 A | 12/1998 | Dordick et al. |
| 6,410,256 B1 | 6/2002 | Ceri et al. |
| 7,267,958 B2 * | 9/2007 | Dordick et al. ................. 435/7.1 |
| 2002/0025537 A1 | 2/2002 | Bylina et al. |
| 2002/0160444 A1 | 10/2002 | Reynolds et al. |
| 2006/0073470 A1 | 4/2006 | Noda et al. |
| 2007/0042453 A1 | 2/2007 | Novak et al. |
| 2008/0166753 A1 * | 7/2008 | Storey et al. .................... 435/32 |

FOREIGN PATENT DOCUMENTS

| EP | 0242305 A1 | 10/1987 |
| WO | WO 2007053561 A2 * | 5/2007 |

OTHER PUBLICATIONS

Uppuluri et al., Dispersion as an Important Step in the *Candida albicans* Biofilm Development Cycle, PLoS Pathogens, 2010, 6(3), 1-13.*
BD Diagnostic Systems, Instructions for Use—Ready-to-Use Bottled Media, 2003, 1-3.*
Pierce et al., A Simple and Reproducible 96 Well Plate-Based Method for the Formation of Fungal Biofilms and its Application to Antifungal Susceptibility Testing, Nat. Protoc., 2008, 3(9), 1494-1500.*
DiDone et al., A Novel Assay of Biofilm Antifungal Activity Reveals That Amphotericin B and Caspofungin Lyse Candida Alibicans Cells in Biofilms, Yeast, 2011, 28, 561-568.*
International Search Report for PCT Application No. PCT/US2011/021407 issued Sep. 26, 2011.
Written Opinion for PCT Application No. PCT/US2011/021407 issued Sep. 26, 2011.
International Preliminary Report on Patentability for PCT Application No. PCT/US2011/021407 issued Jul. 17, 2012.
Eun, Ye-Jin and Weibel, Douglas B. (2009) "Fabrication of microbial biofilm arrays by geometric control of cell adhesion." Langmuir 25 (8), 4643-4654.
Jagnow, Jennifer and Clegg, Steven. (2003) "*Klebsiella pneumoniae* MrkD-mediated biofilm formation on extracellular matrix- and collagen-coated surfaces." Microbiology, 149, 2397-2405.
Xu, Tao, et al. (2004) "Construction of high-density bacterial colony arrays and patterns by the ink-jet method." Biotechnology and bioengineering 85 (1), 29-33.

* cited by examiner

*Primary Examiner* — Maria Leavitt
*Assistant Examiner* — Amy M Bunker
(74) *Attorney, Agent, or Firm* — Thomas Horstemeyer, LLP

(57) ABSTRACT

In one embodiment, a testing device includes a substrate and a plurality of spatially distinct fungal cultures disposed on the substrate.

13 Claims, 1 Drawing Sheet

DEVELOPMENT OF A HIGH-THROUGHPUT SCREEN FOR THE IDENTIFICATION OF NOVEL ANTIFUNGAL DRUG CANDIDATES

CROSS-REFERENCE TO RELATED APPLICATION

This application is the 35 U.S.C. §371 national stage of PCT Application No. PCT/US2011/021407, filed Jan. 14, 2011, which is herein incorporated by reference in its entirety and which also claims priority to, and the benefit of, U.S. Application 61/295,428, filed Jan. 15, 2010, which is herein incorporated by reference in its entirety.

BACKGROUND OF THE INVENTION

1. Field of the Invention

The invention generally relates to biochemical/microbiological testing methodologies. More particularly, the invention relates to antifungal screening tests.

2. Description of the Relevant Art

Nosocomial (hospital acquired) infections are the fourth leading cause of death in the U.S. with 2 million cases and more than $5 billion in added medical cost per annum. A large number of these infections are fungal infections, and are often associated with implantable devices, intravascular and urinary catheters, orthopedic implants, and intrauterine contraceptive devices, which is an $180b per year industry. Fungal infections are much more lethal than bacterial infections as seen by mortality rates ~50% for candidiasis, 90% for aspergillosis, and 100% for zygomycosis. For example, in pediatric patients, candidiasis (the most common fungal infection) is associated with a 10.0% increase in mortality, a mean 21.1-day increase in length of stay, and a mean increase in total per-patient hospital charges of $92,266. Similarly, in adult patients candidiasis is associated with a 14.5% increase in mortality, a mean 10.1-day increase in length of stay, and a mean increase in hospital charges of $39,331. Overall, these numbers suggest that despite having a market of $3.1b per year, which is ~10% of all anti-infectives, currently used antifungals are still ineffective. There are no new effective drugs in sight, and the antifungal pipeline is mostly dry.

A major reason for poor efficacy of antifungal treatments is most fungal organisms grow as 'biofilms' on surfaces of implantable medical devices, and the biofilms are significantly less susceptible to antifungal drugs compared to free-floating or planktonic cells. Biofilm infections are notoriously difficult to treat, and they commonly manifest as chronic or recurrent infections, and constitute a number of clinical challenges.

Biofilms are complex three-dimensional structures, which are composed of different morphological forms of the organism including yeast, pseudohyphae and hyphae, in an extracellular matrix. The antifungal resistance of biofilms is primarily attributed to changes in genetic, physiological and molecular characteristics of the cells in the biofilm, and secondarily to slow diffusion of drugs, and the binding of drugs to the biofilm matrix. Thus, there is a need to develop new strategies for the screening and discovery of antifungal drugs that prevent or control the formation of biofilms. The current industry standard is 96-well plate assay, which, when invented in 2001 was revolutionary and it changed the way fungal biofilms were examined. Prior to 2001, growth and characterization of fungal biofilms was an ordeal, and was performed by only a handful of investigators by mostly forming one biofilm at a time. However, practical considerations of time, cost and reagent volume severely limit the use of 96-well plate assays for probing diverse set of chemical libraries containing tens of thousands of molecules for new drugs, and novel, innovative technologies are sorely needed.

SUMMARY OF THE INVENTION

In one embodiment, a novel tool for screening antifungal compounds that can be used to identify new potential antifungal drugs has been developed.

In one embodiment, a testing device includes a substrate and a plurality of spatially distinct fungal cultures disposed on the substrate. The substrate, in some embodiments, includes a hydrophobic coating. At least one of the plurality of spatially distinct fungal cultures may include a fungus embedded in a matrix.

The testing device may be used for testing of one or more compounds for antifungal activity. In use, a compound is allowed to interact with one or more spatially distinct fungal cultures disposed on the substrate. The interation of the compound with the one or more spatially distinct fungal cultures is monitored for antifungal activity.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
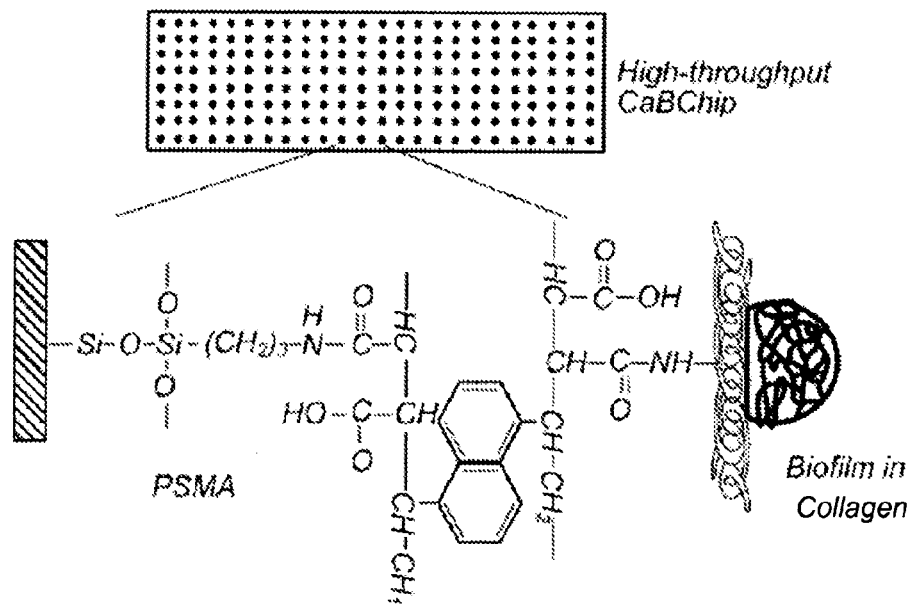
FIG. 1 depicts a schematic diagram of a biofilm encapsulated in collagen attached to a PSMA-modified substrate.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise.

In one embodiment, a Fungal Biofilm Chip for high-throughput screening (HTS) of antifungal drug candidates, is a microarray-based technology. The advantages of HTS are miniaturization and automation, which combine to cut reagent use and analysis times, minimize or eliminate labor intensive steps, and dramatically reduce assay costs. Such a chip may speed up the drug discovery process by enabling rapid, convenient and inexpensive screening of hundreds-to-thousands of compounds simultaneously. These chips may be used to identify effective drug candidates by screening of large libraries of small molecule compounds.

In one embodiment, *Candida albicans* (the major human fungal pathogen) is used in a *Candida albicans* Biofilm Chip.

In one embodiment, a chip comprises at least 768 spatially distinct fungal cultures, each having a volume of less than 100 nL. In an embodiment, the spatially distinct fungal cultures are disposed on a standard 1"×3" glass slide, although any size substrate may be used. Use of a glass substrate may facilitate optical testing methodologies. In an embodiment, each of the spatially distinct fungal cultures may be tested with a different compound, allowing high throughput screening of the compounds. Thus, compared to current industry standard 96-well plate, the chip embodiments will substantially cut down assay duration and cost, increase reliability, thus enabling high-throughput screening of the small molecule libraries for compounds, which can be advanced as novel antifungal agents. Table 1 depicts a comparison of the features of a 96-well plate to an embodiment of antifungal chip.

TABLE 1

Comparison of current industry standard with our screening technology

| Attribute | 96-well plate | Fungal Chip |
| --- | --- | --- |
| Volume | 100-200 µl | 10-100 nl |
| Cell number (approximate) | 100,000 per well | 200-500 per spot |
| Sample size | 96 per plate | up to 2,000 per chip |
| Liquid handling | Manual pipetting | Automated dunk and rinse |
| Analysis | Colorimetric-XTT | Fluorescence with microarray scanner |
| Duration single run | 48 h | 18 h[a] |
| Cost per assay[b] | $1.32 | $0.18 |
| Estimated time to "hits"[c] | 8-12 months | 1 month |
| Estimated time from "hits to leads"[d] | 12 months | 3 months |

[a] estimated
[b] estimated cost per assay taking into account laboratory supplies and reagents, cost of drug, instrument use, and technician time.
[c] refers to time devoted for "primary" screening at a singled fixed concentration for a library of 20,000 compounds.
[d] refers to time for secondary screenings (dose response, screening analogues, initial PD and PK studies) for an estimated 120 hits for the identification of the most promising "leads" (1-5 compounds) to constitute candidates for drug development.

Described herein are a method and system for conducting high-throughput, microscale testing for antifungal agents. In use, a reaction between a drug and a spatially distinct fungal culture may be used to identify new drugs that are effective antifungal agents. For example, if a reaction between fungi at a predetermined location are killed or otherwise undergo a measurable physiological or morphological change by the compound delivered to the location, it indicates that the compound will likely have an effect (e.g., toxicity) on the type of fungi at the specific location. The testing device, for example, may be used to optimize a potential drug candidate or pharmacophore to improve its efficacy and/or reduce its side effects. For example, a promising antifungal compound, and various derivatives of the antifungal compound, may be applied to the different portions of the substrate. A reaction between a compound and fungi at a predetermined location can be used to identify the most promising drug candidates.

The testing device includes a substrate and a plurality of spatially distinct fungal cultures disposed on the substrate. The substrate may be formed from any material that is compatible with fungal cultures, or that may be modified to be compatible with fungal cultures. Examples of suitable substrates include a semiconductor wafer (e.g., a silicon substrate), a glass or quartz microscope slide, a metal surface, or a polymeric material (e.g., PDMS, PTFE, polystyrene). In an embodiment, solid support is a flat, thin solid, such as a glass/quartz microscope slide or a silicon wafer.

In an embodiment, the substrate may be treated with an adhesion material to improve adhesion of the fungi culture to the surface of the substrate. In one embodiment, a hydrophobic polymer may be applied to the substrate (e.g., glass/quartz slide, silicon wafer, polymeric slide, etc.). For purposes of the present disclosure a polymer is considered to be hydrophobic or water-insoluble if it is "sparingly soluble" or "practically insoluble" or "insoluble" as defined by USP 29/NF 24. Examples of hydrophobic polymers include, but are not limited to, acrylic acid-based polymers, methacrylic acid based polymers, and acrylic acid—methacrylic acid based copolymers, and polyolefins (e.g., polystyrene) and modified polyolefins (e.g., polystyrene-co-maleic anhydride (PSMA). Other adhesion materials include siloxane adhesive materials. For example, amino-siloxanes (e.g., 3-aminopropyltriethoxysilane) may be used to improve adhesion of fungi to the slide. In one embodiment, a combination of a siloxane adhesive material and a hydrophobic polymer is used to treat a substrate prior to adhesion of the fungi.

Other materials that may be used to coat a substrate include, but are not limited to, proteins (collagen, poly-L-lysine), carbohydrates (hyaluronic acid), peptide tethers, and exopolysaccharide components of a biofilm matrix.

In some embodiments, the fungi may be encapsulated or adhered to the surface of a matrix material. The material of a matrix may be permeable to small molecules, including potential drug candidates. Each matrix can be the same or different material. The matrix material can be substituted or unsubstituted and includes a solgel, a hydrogel, a polyacrylamide, a polyacrylate, a polyvinyl alcohol, polyvinylene, or a polyvinyl silicate, such as a polyacrylate substituted with a sugar comprising sucrose, glucose, galactose, trehalose, mannose, or lactose. In another embodiment, the matrix material is a substituted or unsubstituted solgel.

A solgel, for example, is a tetramethoxyorthosilicate, a methyl-trimethoxyorthosilicate, a tetraalkoxyorthosilicate, or a trialkoxyorthosilicate. A hydrogel is, for example, a polyacrylamide, a polyacrylate, a sugar-substituted polyacrylate, polyethylene glycol (PEG), a polyvinyl alcohol or a natural hydrogel (collagen, matrigel). A polysaccharide gel is, for example, an alginate, a dextran, a starch, a cellulose, a carrageenan, a poly(hyaluronic acid), a heparin, a guar, or an inulin. Other polymers include a polyvinylene, a poly(vinyl acetate), a poly(ethyl vinyl ether, a polyacrylate such as a polymethyl methacrylate, a polystyrene, a polyvinyl silicate, a polyurethane, a polyalkanoate, a poly(lactic acid), a poly (3-hydroxybutyrate), or substituted variations thereof.

Encapsulation means the fungi is at least partially contained within the volume of a matrix material. Encapsulation within the volume of a matrix often maintains the activity of the fungi better than surface immobilization. Furthermore, the volume of a matrix can contain more fungi than can be attached to a surface area equal to the footprint of a matrix. Depending on the matrix material, fungi may be physically trapped or caged, and/or can be covalently attached by a chemical bond, or tethered.

Appropriate matrix materials, and encapsulation of compositions therein, are described in the literature, including U.S. Pat. Nos. 5,854,030; 5,618,933, and 5,474,915, all of which are incorporated herein by reference.

Individual spatially distinct fungal cultures may be placed on the substrate using manual pipetting or a robotic microarray spotter. A robotic microarray spotter can be used in a number of ways relevant to the invention, including to prepare arrays of fungi cultures on a surface of the substrate. Of the many commercial spotters available, there are, for example, contact pin spotters such as the GeneTAC G$^3$ (Genomic Solutions, Lansing, Mich.), OmniGrid (Digilab) and piezoelectric (inkjet mechanism) spotters such as the NANO-PLOTTER NP1.2® (GeSiM mbH, Grosserkmansdorf, Germany).

In use, the testing device may be used to search for new antifungal compounds. A plurality of potential antifungal compositions (testing compositions) may be applied to one or more of the fungi at predetermined locations. Interaction of the potential antifungal composition with the fungi at the predetermined location may be monitored. The compounds that exhibit the highest antifungal activities may be identified based on the locations exhibiting the most effective antifungal abilities. In one embodiment, an applied testing composition may include a hydrogel, a protein gel, a polysaccharide gel, a cellulose, a gelatin, a polystyrene, or a polyacrylamide. Examples of hydrogels that may be included in the testing composition include, but are not limited to, polyvinyl alcohol, collagen, carrageenan, poly(hyaluronic acid), and inulin. In a preferred embodiment, the applied composition includes collagen. The applied composition may be added manually or using a robotic microarray spotter.

The volume of applied composition solution added should be optimized to provide efficient wetting of each matrix and enable effective partitioning of the applied composition into the matrix. For example, the volume of the applied composition solution added can be between about 0.2 and about 5 times the volume of each matrix. Alternatively, the volume of the applied composition solution added can be between about 0.5 and about 2 times the volume of each matrix.

In an embodiment, the testing system includes a detector. A detector assays a desired feature, i.e., physical, chemical, or biological evidence of reactions, (e.g., color changes, changes in fluorescence, etc.). Examples of detectors include, but are not limited to an electrode, an aspiration probe, a laser desorption probe, an ion beam desorption probe, a gas desorption probe, a liquid desorption. probe, a contact probe, an optical spectrometer, a microscope, an imager, a mass spectrometer, a chromatography apparatus, an electro chemical detector, a particle detector, a chemical affinity detector, a radiation detector, a magnetic resonance spectrometer, or the components to perform a cell proliferation assay, a cytotoxicity assay, an immunoassay, a binding assay, or a staining assay. Some of the components comprised by the detector, such as the various probes, are not necessarily detectors per se but function to remove a sample and direct it to another component of the detector.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In one embodiment, a fungal chip comprises 'miniaturized' fungal biofilms (e.g., *C. albicans*-) on a standard glass slide. The chip may satisfy one or more of the following criteria: (i) firmly holds hundreds of spatially distinct biofilms on a single glass slide; (ii) forms a 'true' biofilm, that, though small, should contain all the different morphological forms of the fungi (e.g., yeast, pseudohyphae and hyphae) growing in three dimensions; (iii) does not dry easily, allowing cells to be cultured with ease; (iv) does not detach from the substrate against multiple washings; and (v) is amenable for analysis with standard microarray scanner.

In one embodiment, cell-adhesive islands are formed on a non-adhesive, modified glass substrate so that the fungi will attach and grow on these islands, yielding a chip with defined array pattern. This may be accomplished by the following steps in sequence: (i) modifying glass slides by coating with hydrophobic (or other) polymer; (ii) spotting fungi cells encapsulated (or not) in a polymerizable hydrogel or matrix dissolved in cell culture media; (iii) growth at 37 C in a humidified chamber; and (iv) monitoring the growth of cells in the spots using suitable live stain.

In one example, low density *C. albicans* biofilm chips (48 spots per slide) consisting of 500 nL spots, using a hand-held pipette were prepared. *C. albicans* strain SC5314 cell suspension in RPMI medium ($4 \times 10^6$ cells/ml final concentration) was mixed with rat tail collagen I (BD Biosciences; 2 mg/ml final concentration) in 0.01 N NaOH (Sigma). The mixture was kept in ice, and 500 nL was rapidly spotted on polystyrene coated glass slides (Ted Pella) in a regular pattern. The slides were incubated in a humidified chamber at 37° C. for 24 h. After growth, the slides were stained with fungal stain FUN1 (Molecular Probes), which stains live cells. The slides were analyzed both using a microarray scanner, and also by confocal microscopy. We were able to produce patterns that were distinct and robust, able to withstand multiple washes, and had all the morphological forms of fungi indicating that it is indeed a true biofilm.

A high-throughput product may also be prepared. A robotic microarrayer (Microsys, Digilab) may be used to spot 50 nL spots of fungal cells on glass slides in a regular pattern of 48 rows×16 columns, thus producing 768 distinct biofilms on a single chip. Polystyrene-co-maleic anhydride (PSMA) and/or other coating materials, instead of polystyrene slides, may be used to improve adherence of biofilm spots. In an example, glass slides are cleaned thoroughly with 70% ethanol to remove any dust particles, acid-cleaned by sulfuric acid wash for 1 h, thoroughly washed with water, rinsed with acetone and blow-dried. The slides are spin-coated with 0.1% polystyrene-co-maleic anhydride (PSMA) in toluene, and air-dried. The basis for using PSMA functionalized slides and collagen spots is that, while the polystyrene moiety of PSMA provides a uniform hydrophobic surface, the maleic anhydride moiety covalently bonds to the amino group of lysine of collagen. Other combination of coatings are also possible. This arrangement provides defined cell-adhesive islands on a cell non-adhesive background. Second, in order to prevent gelation of collagen during spotting, 50 nL of 0.01 N NaOH is spotted on the chip, and then acidic collagen is spotted on top resulting in in situ, on chip gelation. Culture time is 24 h, but may be reduced to 12 h or 6 h.

The initial series of experiments have used *C. albicans* as a model organism to provide "proof of concept". However, this technology should also be amenable to grow of other fungal organisms (i.e. *Aspergillus fumigatus, Cryptococcus neoformans, Zygomycetes*) and also bacterial pathogens (i.e. *Staphylococcus aureus, Pseudomonas aeruginosa* and others), and may include organisms growing as biofilms and/or free living organisms.

Figure 2:
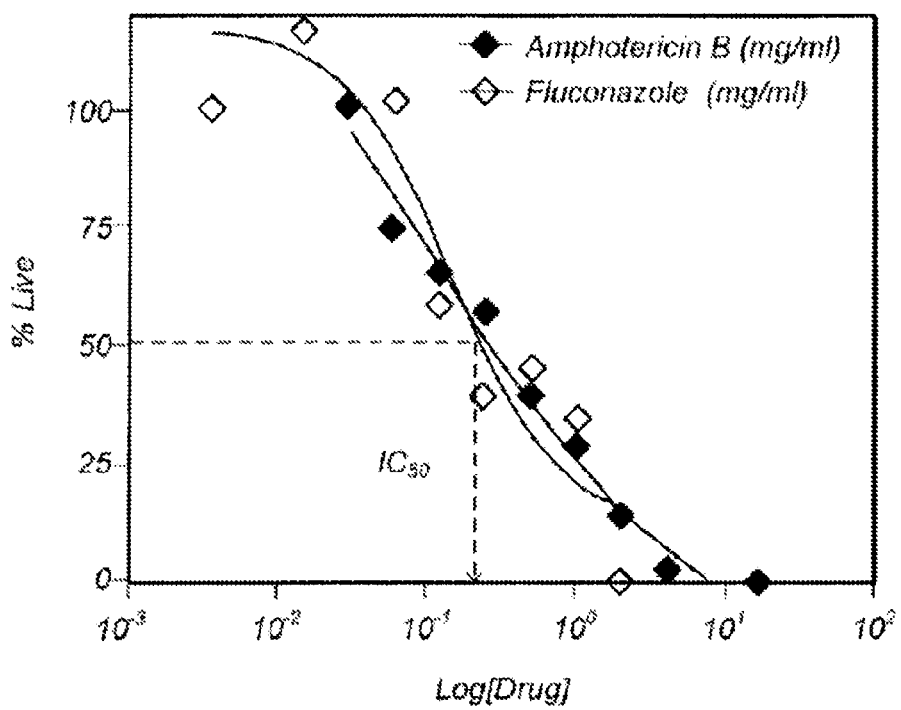
FIG. 2 depicts a graph of drug concentration vs. active fungi during testing of Amphotericin B and Fluconazole.

In one embodiment, the chip is used for high throughput screening of libraries of compounds to identify those that display antifungal activity. In one example, amphotericin B, fluconazole, and caspofungin were tested using the chip at different concentrations. After formation of the individual biofilms on the chip, the biofilms were exposed to different concentrations of these compounds for 24 hr. After this, the slides were washed by gently dunking in PBS (Sigma). The slides were then stained with FUN1, dried and read using a scanner (GenePix 4100, Molecular Devices). The $IC_{50}$ values were calculated by fitting the Hill equation to the susceptibility data using GraphPad Prism software. These results were also benchmarked by comparing with those obtained using the conventional 96-well plate employing XTT assays, with excellent results (correlation). FIG. 1 depicts a schematic diagram of a biofilm encapsulated in collagen attached to a PSMA-modified substrate. FIG. 2 depicts a graph of drug concentration vs. active fungi during testing of Amphotericin B and Fluconazole using a low density C. albicans biofilm chip.

C. albicans strain SC5314, a well characterized strain from the point of view of biofilm formation, was used throughout a second study. Cells stored at −70° C. as glycerol stocks were propagated by streaking a loopful of cells onto yeast peptone dextrose (YPD) agar (1% [wt/vol] yeast extract, 2% [wt/vol] peptone, 2% [wt/vol] dextrose) and incubated overnight at 37° C. A loopful of cells from YPD agar plates were inoculated into flasks (150 ml) containing 20 ml of YPD liquid media to be grown overnight in an orbital shaker (150-180 rpm) at 30° C. Under these conditions, C. albicans grows as budding-yeasts.

Preparation of Functionalized Slides

Normal microscopic glass slides (1"×3") (Fisher Scientific, Waltham, Mass.) were cleaned extensively to expose the silanol groups (—SiOH) on the surface. First, the slides were placed in a removable slide rack and washed by immersing them in a staining jar containing ethanol. The slides were then wiped clean using paper towels and air-dried using nitrogen gas. Next, the slide rack containing the slides was immersed in a dish filled with concentrated sulphuric acid and incubated for an overnight treatment. Finally, these slides were subjected to sonication and washed with Milli-Q water for 30 min, following another wash in acetone. This treatment exposed the silanol groups on the glass surface.

Clean slides were then coated with 3-aminopropyltriethoxysilane (APTES) (Sigma Aldrich, St. Louis, Mo.), by immersing the slide rack in APTES for 30 min. The slides were baked in the furnace at 110° C. for 15 min. Baking allowed cross-linking of the APTES, resulting in glass slides with its surface expressing functional groups (—$NH_2$—) of APTES. Finally the slides were spin coated with 1% (wt/vol in toluene) Polystyrene-Co-Maleic Anhydride (PS-MA) (Sigma) to achieve a mono-layer of hydrophobic coating.

Optimization and Printing of High Density Fungal Cell Arrays onto Functionalized Glass Slides and Subsequent Biofilm Development A four-factor, two-level factorial design was performed using MINITAB (Minitab Solutions Inc., State College, Pa.) and DESIGN EXPERT (Stat-Ease Inc., Minneapolis, Minn.) software to obtain optimal conditions of media concentration, seeding density, collagen concentration and PSMA coating concentration for wash-resistant biofilm growth on the CaBChip. The response (output) metrics were true biofilm yield and robust attachment, measured using microarray scanner and light microscope. For preparation of inocula for printing and biofilm formation in the CaBChip, cells harvested from overnight YPD cultures were washed twice in sterile phosphate buffered saline (PBS; 10 mM phosphate buffer, 2.7 mM potassium chloride, 137 mM sodium chloride (pH 7.4) (Sigma) by centrifugation at 3000 g. The cells were then resuspended in Reconstruction buffer (0.2N NaOH solution with 2.2% (wt/vol) Sodium Bicarbonate and 4.8% (wt/vol) HEPES). One hundred fold dilutions of the suspended cells were prepared and counted using a hemocytometer on a bright field microscope. Following count, a suspension of cells was prepared in reconstruction buffer at a cell density of $5\times10^7$ cells/mL, which was diluted ten times by addition of 10× RPMI-1640 supplemented with L-glutamine and buffered with morpholinepropanesulfonic acid (Angus Buffers and Chemicals, Niagara Falls, N.Y.) containing collagen (1.8 mg/ml) (Type 1 from rat tail, BD Biosciences, Bedford, Mass.), to give a final concentration of cells of $4\times10^6$ cells/mL. The suspension containing yeast cells, collagen and media was printed (50 nL per spot) on the functionalized PSMA-coated glass slides using a microarray spotter (Omnigrid Micro, Digilab Inc., Holliston, Mass.). Printing was carried out by non-contact deposition using conically tapered 190 μm orifice ceramic tips (Digilab). The resulting spots were approximately 700 μm in diameter, spaced 1.2 mm apart; spots were printed in an array of 48 rows and 16 columns. In a standard print run, the tips were primed, rinsed in running water and vacuum dried twice after each loading and printing step. The cell suspension was kept on ice to prevent the gelation of collagen before printing and agitated gently just prior to placement on the printing robot to ensure a uniformly mixed cell suspension. A relative humidity of 97% was maintained during printing to prevent the drying of the biofilm spots. All microarray operations such as aspiration, dispensing, priming, printing and spatial distribution of array were controlled by AxSys program (Digilab). All surfaces, including the source plate station, wash and vacuum station, vacuum slide platter and printing chamber were sterilized by wiping with 70% isopropanol. In our experience, these procedures ensure that there is no detectable contamination of wells in the plates or of spots on the microarray. Immediately after printing, the slides were placed inside humidifier chambers (ArrayIt Corporation, Sunnyvale, Calif.) which were placed inside a 37 C incubator over different periods of time to allow for biofilm formation.

Assessment of Metabolic Status of Cells within Biofilms

FUN 1 [2-chloro-4-(2,3-dihydro-3-methyl-(benzo-1,3-thiazol-2-yl)-methylidene)-1-phenylquinolinium iodide] (Invitrogen Corp., Carlsbad, Calif.) was used to stain and determine viability (levels of metabolic activity) of C. albicans cells within the biofilms formed in the chips. This membrane-permeable fluorescent dye is internalized and processed by metabolically active fungal cells, and has excitation and emission spectra that are compatible with the sets of lasers and filters installed in most microarray scanners. Briefly, the CaBChip was stained with 0.5 μM FUN 1, by simply dunking the entire CaBChip in a staining jar, and incubated in the dark at 37° C. for 30 min Following incubation, the chip was washed three times by dunking in PBS in order to remove excess stain. The slides were then air-dried and scanned in a microarray scanner (Genepix Personal 4100A, Axon Instruments, Union City, Calif.). A laser of 532 mn with a PMT gain of 270 was used to read the chip and fluorescent intensity of each spot was determined using GenePix 4.1 software (Axon). Fluorescence levels from FUN 1 staining were recorded as Relative Fluorescence Units (RFU). The microarray reader converts the real fluorescence signal into an electronic signal that can be "tuned" using the gain setting or sensitivity setting, and thus RFU is an arbitrary unit. Initial experiments indicated an excellent linear correlation between number of metabolically active cells spotted on the microarray and levels of FUN 1 fluorescence.

Microscopy Techniques

Bright-field light microscopy techniques on an inverted microscope (Fisher Scientific) equipped for photography were used to routinely monitor biofilm formation, as a means of directly visualizing the overall morphology, distribution and topography of biofilms grown in the chip. The images were processed for display using Micron software (Westover Scientific, Bothell, Wash.). For scanning electron microscopy, biofilms formed in the chip were fixed with a solution of glutaraldehyde (2.5% w/v) in 0.1M sodium cacodylate buffer at pH 7.4 for 2 h at 37° C. Following fixation the biofilms were treated with a solution of osmium tetraoxide (1% w/v) in 0.1M sodium cacodylate buffer at pH 7.4 for 2 h at room temperature. The samples were rinsed with water and soaked in a series of ethanol solutions (a step gradient of 30%, 50%, 70%, and 90% in water for 10 min per step), ending with 100% ethanol. After dehydration, the samples were dried overnight in a vacuum dryer and subsequently coated with a 60:40 gold-palladium alloy; approximately 10 nm thick using a Cressington Sputter coater for a duration of 30 sec. Scanning electron microscopy was performed using a Zeiss EVO 40 electron microscope (Carl Zeiss, Thronwood, N.Y.). Confocal Scanning Laser Microscopy (CSLM) of FUN 1 stained biofilms to visualize three dimensional patterns and determine the architecture of the biofilms grown in the chip. CSLM was performed with a Zeiss LSM 510 confocal microscope (Carl Zeiss), using a rhodamine/fluorescein isothiocyanate protocol with excitation at 488 nm (argon ion laser). Images of sections in the xy plane were taken along the z axis, acquired by the resident software and processed using Auto-Quant (Media Cybernetics, Bethesda, Md.) and IMARIS 6.4 (Bitplane, St. Paul, Minn.).

Susceptibility Testing of Cells within Preformed *C. albicans* Biofilms in CaBChip Against Antifungal Agents Susceptibility testing of cells within *C. albicans* biofilms in CaBChip was performed against clinically used antifungal agents amphotericin B and fluconazole. Amphotericin B was obtained as a powder from Sigma (St. Louis, Mo.). A stock solution of Amphotericin B (1.6 mg/ml) was prepared in DMSO and stored at −20° C. until used. Fluconazole was obtained as injection from Sicor Pharmaceuticals, Inc. (Irvine, Calif.). A stock solution of Fluconazole in 0.9% Sodium Chloride solution, available as injection was stored at 4° C. until used. Subsequent dilutions of the antifungals were made in RPMI-1640 media supplemented with L-glutamine and buffered with MOPS. On top of the biofilms formed after 24 h, drugs of desired concentration of equal spot volume (50 nL), in two-fold dilutions were spotted using the robotic microarrayer. The CaBChip(−s) containing drugs were then incubated in a humidified chamber for an additional 24 h, after which the slides were washed by gently dunking them in PBS. Eight different concentrations of the drugs in six replicates, with appropriate positive (no drug) and negative (dead cells) controls were tested on a single CaBChip. Multiple (at least two) chips were processed in parallel. Thus, depending upon the efficacy of the drug and its dose, each spot had different fluorescence levels and by quantifying these values at each spot, susceptibility profiles for each compound were determined. The fluorescence intensity of the control and dead (killed with sodium hypochlorite for 20 min) biofilms were arbitrarily set at 100% and 0% respectively, and the inhibitory effects of compounds were determined by the reduction in fluorescence intensity in relation to the controls, as measured in the microarray scanner. Data was calculated and expressed as percent biofilm inhibition relative to the average of the control wells. $SMIC_{50}$ and $SMIC_{80}$ values for each antifungal were determined as before. The calculated $IC_{50}$ (Inhibitory Concentration of drugs required to reduce the fluorescence intensity by half, compared to live-controls) values were determined by fitting the constant slope Hill equation (an equation determining the non-linear drug dose-response relationship) using GraphPad Prism software (La Jolla, Calif.). For comparison purposes, antifungal susceptibility testing was also performed using the 96-well microtiter plate model of *C. albicans* biofilm formation previously developed by our group, that uses the colorimetric (2,3-bis(2-methoxy-4-nitro-5-sulfo-phenyl)-2H-tetrazolium-5-carboxanilide) (XTT) assay as a measure of viability of cells within biofilms.

Results and Discussion

Traditionally, most models for the formation of *C. albicans* biofilms are cumbersome, requiring expert handling, large volumes, long processing times and the use of specialized equipment not generally available in a regular microbiology laboratory. Frequently biofilms are grown on catheter disks or sheets placed inside a fermentor or a bioreactor under either static or dynamic flow conditions. These culture techniques are slow, complex and demanding, and were mitigated to a great extent by the development of a 96-well microtiter plate model for the formation of *C. albicans* biofilms. In this model, fungal biofilms are formed on the bottom of the wells of microtiter plates, and the ability of metabolically active sessile cells to reduce a tetrazolium salt (XTT) to water-soluble orange formazan compounds, the intensity of which can then be determined using a microtiter-plate reader, is used as a semi-quantitative measurement of biofilm formation. This model was also adapted for antifungal susceptibility testing of cells within the biofilms. However, in this era dominated by high throughput demands and "hunger for speed", the multiwell plate format still suffers from several limitations, most importantly inefficient liquid handling and removal without disturbing the biofilms, which severely limits the automation of this process. Other disadvantages of 96-well microtiter plate model include the need for relatively larger volume of reagents (thereby increasing costs) as well as incompatibility with high content experimentation and image analysis. A microarray format/platform ameliorates all these issues, thus allowing for truly high-throughput applications. Though the microarrays have been used to great benefit in the fields of genomics and proteomics, comparatively little effort has been directed toward using cellular microarrays, particularly in the case of pathogenic microorganisms.

Design and Fabrication of the *Candida albicans* Biofilm Chip (CaBChip)

Our objective was to develop a high density microarray of spatially addressable three-dimensional biofilms of *C. albicans*, which should satisfy the following requirements: (i) firmly hold hundreds of spatially distinct biofilms on a single glass slide; (ii) forms a 'true' biofilm, and though small, displays phenotypic properties comparable to those of regularly-grown biofilms (i.e. growth, morphological and architectural characteristics and increased drug resistance); (iii) does not dry easily so that the cells may be cultured for prolonged periods of time; (iv) attaches robustly to the substrate and does not detach against multiple washings; and (v) fully compatible for analysis with a standard microarray scanner. We first performed a series of proof-of-concept experiments, mostly using manual pipetting prototypes, to check multiple parameters of biofilm formation, including those related to surface chemistry, matrix encapsulation, growth media and inocula preparation. The first requirement was that of a hydrophobic surface, allowing for discrete, independent liquid spots of small volume (in the nanoliters range) to be deposited on the surface of the microscope slide. Thus, the borosilicate (glass) slides were first pre-treated with 3-aminopropyltriethoxysilane (APTES), followed by coating with polystyrene-co-maleic anhydride (PSMA). The styrene-co-maleic anhydride molecules zip together forming a monolayer made of two molecules in cross section, thus enhancing the hydrophobicity of the substrate. The PSMA also provides sufficient functionality for subsequent covalent binding to an encapsulating matrix such as collagen. The use of an encapsulating matrix was deemed necessary since initial experiments indicated that, in order to form robust (capable of withstanding the multiple washing steps) *C. albicans* biofilms on the microscope slides, it was required to encapsulate the fungal cells within a matrix. The use of collagen as the matrix of choice was mostly due to its optimal and easily controllable gelation characteristics, covalent binding to the functionalized surface, and the fact that it represents a biological substrate that mimics the tissue extracellular matrix in vivo. Next, using a two-level factorial design, we found the optimal operating parameters namely, concentrations of collagen, PSMA, *C. albicans* seeding density and growth media, that maximized the biofilm yield on spots that are stably attached to the substrate. We observed that (i) high collagen concentration did not favor filamentation, and cells remained in planktonic form; and, on the other hand, low collagen concentration did not favor robust attachment of spots; (ii) excessively rich media resulted in hyper-filamentation forming a pseudo-biofilm, and poor media did not promote sufficient cell growth; (iii) high seeding density did not favor biofilm formation; and (iv) high PSMA coating concentration promoted stable attachment of spots. Hence, we concluded that a collagen concentration of 1.8 mg/ml with cell seeding density $4 \times 10^6$ cells/ml in a 4× RPMI media printed on 0.1% PSMA-coated surfaces will yield most optimal biofilm chip. Finally, we printed the high density arrays using a robotic microarrayer. We robotically spotted a total of 768 spots of 50 nL each, containing a suspension of *C. albicans* yeast cells in collagen and microbiological media. This resulted in hemispherical spots that were 700 μm in diameter, with a spot-to-spot distance of 1.2 mm. After initial printing, the slides are simply incubated under inside humidifying chambers (to prevent drying) at 37° C. to allow for biofilm development. No additional media was added to the biofilm chip after initial spotting, which is in stark contrast with most models in which biofilms are submerged in large volumes of media. The extent of biofilm formation was assessed using FUN 1, a simple and sensitive assay for fluorescent staining of metabolically active fungal cells, which is fully compatible with standard microarray scanners.

Growth Characteristics and Morphological and Architectural Features of *C. albicans* Biofilms in the CaBChip By using conventional methods for *C. albicans* biofilm formation, it is well established that the process of biofilm development occurs through different phases, including initial adherence of cells to a substrate, followed by growth and proliferation (which in the case of *C. albicans* is intimately associated with filamentation), and a final maturation phase that also includes accumulation of the extracellular matrix. To further establish the kinetics of biofilm formation in the chip format, we monitored the growth of viable cells in collagen gel spots on the CaBChip over time using both microscopy and FUN 1 staining. This fluorescent dye is processed biochemically in the cytoplasm of living cells, forming cylindrical intravacuolar structures and rendering a fluorescent signal that can be read with a regular microarray reader using the appropriate excitation and emission filters. Similar to regular biofilms, direct bright-field microscopic observations revealed that *C. albicans* biofilms formed in the CaBChip are composed of yeast, pseudohyphae and hyphae. The results from these series of experiments indicated that, after a somewhat extended lag time of about 4 hours, cells grew rapidly and developed biofilms with maximum readings observed at approximately 12-18 h for what seem to be fully developed, complex biofilms. After 18 h, there was a reduction in the metabolic activity of biofilm cells, thus indicating that biofilms had reached maturity. Thus, it would seem that, compared to other standard methods in which formation of mature biofilms typically occurs over 24-48 h and beyond, the process of biofilm development and maturation is somewhat accelerated in the chip, most likely due to the sub-microliter volume range, which in turn may result in faster nutrient depletion and accumulation of metabolic waste.

In order to further ascertain the morphological and architectural characteristics of biofilms in the CaBChip, we used SEM and CSLM. SEM provides a visual description of the biofilms at higher magnification. At the highest magnification it was seen that the fungal hyphae are embedded within the matrix of collagen fibers, which are approximately 2μm and 100 nm in diameter, respectively. Contrary to SEM, the non-destructive nature of CSLM allows for the visualization of biofilms in its native state. Results of FUN 1-stained biofilms using CSLM indicate that the biofilms formed in the CaBChip show spatial heterogeneity, with regions of metabolically active cells interspersed within the extracellular matrix, which is not stained by the metabolic dye. The thickness of the biofilm was estimated to be approximately 50 μm. Thus, from the point of view of their morphological, structural and architectural properties and despite several thousand-fold miniaturization, the nano-scale biofilms formed on the CaBChip display phenotypic characteristics that are comparable to *C. albicans* biofilms formed using standard methodologies.

Validation of the CaBChip for High-throughput Analyses and Antifungal Susceptibility Testing An important aspect of a high density array is the ability to make multiple measurements at a single time. Thus, it is imperative to demonstrate that all *C. albicans* biofilms formed in a same CaBChip are equivalent to each other, which is essential for its future use in large scale high throughput/high content screening applications. To this end, we optimized the viability stain FUN 1 and operating parameters of the microarray scanner such that the fluorescence intensity correlated linearly with cell number over the range of interest. We also found that the fluorescent intensities from spots that are seeded at same initial cell density were statistically indistinguishable indicating uniform distribution of biofilms at different locations on the CaBChip. This demonstrates that the CaBChip is a valid microarray-based platform for high-throughput screening techniques, including drug discovery or the screening of large collections of mutant strains, that will allow for the genetic dissection of the biofilm developmental process.

From a clinical perspective, one of the main negative consequences of biofilm formation is the high levels of antifungal drug resistance against most clinically used antifungal agents exhibited by *C. albicans* cells within biofilms. This is one of the major contributors to the unacceptably high morbidity and mortality rates associated with candidiasis, despite of $3 billion per year spent on antifungal medications in the US alone. Thus, there is an urgent need for the development of new and improved antifungal therapies, and the process of biofilm formation represents a very attractive target. In order to ascertain the functionality of CaBChip in determining the susceptibility profiles of antifungal drugs against pre-formed biofilms, we carried out antifungal susceptibility testing of 24 h *C. albicans* biofilms grown on CaBChip against fluconazole and amphotericin B. Using the robotic arrayer, drug concentrations of double-increments were spotted on top of the mature pre-formed biofilms on CaBChip and incubated for an additional 24 h period, after which time FUN 1 was added. The fluorescence intensity of control (no drug) and sodium hypochlorite-treated dead biofilms were arbitrarily set at 100% and 0% respectively, and the inhibitory effects of the antifungal agents were determined by the reduction in fluorescence intensity in comparison to the controls. As in the case of biofilms formed using regular methods (i.e. 96 well microtiter plate model), we observed that the biofilms formed on CaBChip were intrinsically resistant to fluconazole with $SMIC_{50}$ and $SMIC_{80}$ values of >1,024 μg/ml. The calculated $IC_{50}$ for fluconazole was >1,024 μg/ml. Also similar to regularly formed *C. albicans* biofilms, amphotericin B was effective against biofilms formed on CaBChip, but only at relatively high concentrations. The calculated $IC_{50}$ for amphotericin B was 0.27±0.041 μg/ml, and the $SMIC_{50}$ and $SMIC_{80}$ values were 0.5 and 1 μg/ml, respectively. These results are consistent with those previously reported for biofilms formed using conventional techniques and once again further corroborate that, despite a near 2,000-fold miniaturization (compared to biofilms formed using the conventional 96-well microtiter plate model), the nanoscale biofilms on the CaBChip display phenotypic properties, including high levels of antifungal drug resistance, that are similar to those formed using standard techniques.

In summary, we have successfully developed a cell-based high density microarray, CaBChip, for the formation of *C. albicans* nano-biofilms. Besides providing cell-specific islands on the substrate, the hydrophobic coating on the CaBChip allows for an increased number of spots that could be printed in a microscope slide. In addition, the choice of a suitable hydrogel, as a "matrix" that encapsulates the individual biofilms, determines the robustness of the chip. Maintaining the integrity of the gel and controlling the adhesion of the matrix onto the substrate are critical for the robustness and performance of the chip. Despite nanoliter volume, the resulting biofilms demonstrate phenotypic characteristics that are consistent with the *C. albicans* biofilm mode of growth. The technology is flexible and we are currently adapting it to other fungal and bacterial organisms. Thus, the CaBChip is truly high-throughput: it employs nano-scale cultures, enables rapid and easy handling, is amenable to automation and fully compatible with standard microarray technology and equipment. In its current format, a single CaBChip replaces up to eight 96-well plates, and multiple chips can be printed and processed simultaneously. By virtue of its miniaturization and automation, the use of this technology platform minimizes manual labor, cuts reagents use and drastically reduces assay costs. By enabling rapid, convenient and inexpensive screening of hundreds-to-thousands of compounds simultaneously, the use of CaBChip in high-content screening applications has the potential for changing the face of the antifungal drug discovery process.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A fungal biofilm testing device comprising:
   a flat substrate having a flat surface comprising a hydrophobic adhesion material coupled to the flat surface, wherein the hydrophobic adhesion material is selected from the group consisting of: a siloxane, an amino siloxoane, a methacrylic acid copolymer, a polyolefin, a polystyrene-co-maleic anhydride (PSMA), and a combination of one or more of these materials; and
   a plurality of spatially distinct spots of fungal cultures disposed on the hydrophobic adhesion material, wherein the spots of fungal cultures are three dimensional and comprise a mixture of fungal cells, a matrix material comprising a collagen hydrogel or an alginate hydrogel, and a growth medium, wherein a viable fungal biofilm, encapsulated in the matrix material, forms in the spots within 6-24 hours of incubation, and wherein the viable, encapsulated fungal biofilms are obtained and capable of remaining viable for at least 24 hours without adding growth media to the flat substrate or submerging the spots on the flat substrate in growth media.

2. The fungal biofilm testing device of claim 1, wherein the substrate comprises a hydrophobic, hydrophilic or amphiphilic coating.

3. The fungal biofilm testing device of claim 1, wherein the substrate is a glass or polymeric substrate.

4. A method of testing a compound for antifungal activity comprising:
   providing a testing device, the testing device comprising: a flat substrate having a flat surface; a hydrophobic adhesion material coupled to the flat surface, wherein the hydrophobic adhesion material is selected from the group consisting of: a siloxane, an amino siloxoane, a methacrylic acid copolymer, a polyolefin, a polystyrene-co-maleic anhydride (PSMA), and a combination of one or more of these materials; and a plurality of spatially distinct spots of fungal cells disposed on the adhesion material, wherein the spots of fungal cultures comprise a mixture of fungal cells, a matrix material comprising a collagen hydrogel or an alginate hydrogel, and a growth medium;
   incubating the device for 6-24 hours to obtain viable fungal biofilms encapsulated within the matrix material in the spatially distinct spots without adding growth media to the flat substrate or submerging the spots on the flat substrate in growth media;
   exposing the compound to the spots on the device; and
   monitoring the one or more fungal biofilms for antifungal activity.

5. A method of making a testing device, the method comprising:
   obtaining a substrate having a flat surface;
   forming a hydrophobic adhesion layer on the flat surface, wherein the hydrophobic adhesion material is selected from the group consisting of: a siloxane, an amino siloxoane, a methacrylic acid copolymer, a polyolefin, a polystyrene-co-maleic anhydride (PSMA), and a combination of one or more of these materials;
   spotting a mixture comprising fungi cells, matrix material comprising a collagen hydrogel or an alginate hydrogel, and growth medium on the hydrophobic adhesion layer to form an array of spatially distinct, three-dimensional spots of fungal cultures disposed on the flat surface of the substrate; and placing the spotted substrate in a humid environment to form viable, encapsulated fungal biofilms in the matrix material in the spots without adding growth media to the flat substrate or submerging the spots on the flat substrate in growth media.

6. The method of claim 5, further comprising forming a hydrophobic, hydrophilic or amphiphilic coating on the substrate prior to adding the fungi cells to the substrate.

7. The fungal biofilm testing device of claim 1, wherein each fungal culture has a volume in a nanoliter range.

8. The fungal biofilm testing device of claim 7, wherein each fungal culture is approximately 100 nL or less in volume upon disposition.

9. The method of claim 5, wherein each fungal culture has a volume in a nanoliter range.

10. The method of claim 9, wherein each fungal culture is approximately 100 nL or less in volume upon disposition.

11. The fungal biofilm testing device of claim 1, wherein the fungal cultures have one or more phenotypic characteristics of a fungal culture biofilm.

12. The method of claim 5, wherein the fungal cultures have one or more phenotypic characteristics of a fungal culture biofilm.

13. The method of claim 4, wherein the compound is added to the spatially distinct fungal culture in a volume of between 0.2 and 5 times a volume of the matrix material for each spot.

* * * * *